(12) United States Patent
Nur et al.

(10) Patent No.: US 10,962,537 B2
(45) Date of Patent: Mar. 30, 2021

(54) BIOCOMPATIBLE POLYMERIC MEMBRANES

(71) Applicant: Memphasys Limited, Homebush (AU)

(72) Inventors: Hani Nur, Kellyville (AU); Sandra Kentish, Kew East (AU); Martin Van Koeverden, Clifton Hill (AU); Vikram Chaudhari, Harris Park (AU)

(73) Assignee: Memphasys Limited, New South Wales (AU)

( * ) Notice: Subject to any disclaimer, the term of this patent is extended or adjusted under 35 U.S.C. 154(b) by 116 days.

(21) Appl. No.: 16/095,653

(22) PCT Filed: Apr. 21, 2017

(86) PCT No.: PCT/AU2017/050361
§ 371 (c)(1),
(2) Date: Oct. 22, 2018

(87) PCT Pub. No.: WO2017/181240
PCT Pub. Date: Oct. 26, 2017

(65) Prior Publication Data
US 2019/0128883 A1   May 2, 2019

Related U.S. Application Data

(60) Provisional application No. 62/326,331, filed on Apr. 22, 2016.

(51) Int. Cl.
*B01D 57/02* (2006.01)
*B01D 69/02* (2006.01)
(Continued)

(52) U.S. Cl.
CPC .......... *G01N 33/561* (2013.01); *B01D 57/02* (2013.01); *B01D 69/02* (2013.01); *B01D 69/10* (2013.01);
(Continued)

(58) Field of Classification Search
None
See application file for complete search history.

(56) References Cited

U.S. PATENT DOCUMENTS 6,328,869 B1 *  12/2001  Ogle .................... B01D 61/44
                                                          204/600
2003/0000836 A1 *  1/2003  Wang ................... A61B 5/4088
                                                          204/452

(Continued)

FOREIGN PATENT DOCUMENTS

EP         0 966 998 A2    12/1999
WO    WO 2018/071978 A1    4/2018

OTHER PUBLICATIONS

Heang et al, "Wide-Range Stiffness Gradient PVA/HA Hydrogel to Investigate Stem Cell Differentiation Behavior," Acta Biomaterialia 35 (2016) 23-31.*

(Continued)

*Primary Examiner* — Salil Jain
(74) *Attorney, Agent, or Firm* — Morse, Barnes-Brown & Pendleton, P.C.; Lisa M. Warren, Esq.; Stanley F. Chalvire, Esq.

(57) ABSTRACT

The present invention relates to polymeric membranes. In particular, the present invention relates to the use of membranes comprising polyvinyl alcohol in electrophoresis.

9 Claims, 10 Drawing Sheets

(51) Int. Cl.
  B01D 71/44      (2006.01)
  B01D 67/00      (2006.01)
  B01D 71/38      (2006.01)
  C07K 1/26       (2006.01)
  G01N 33/561     (2006.01)
  B01D 69/10      (2006.01)
  B01D 71/52      (2006.01)

(52) U.S. Cl.
  CPC ............ *B01D 71/38* (2013.01); *B01D 71/44* (2013.01); *B01D 71/52* (2013.01); *C07K 1/26* (2013.01); *B01D 2325/20* (2013.01); *B01D 2325/28* (2013.01)

(56) References Cited

U.S. PATENT DOCUMENTS

| | | |
|---|---|---|
| 2003/0026752 A1 | 2/2003 | Allan |
| 2003/0047455 A1 | 3/2003 | Ryan et al. |
| 2003/0226752 A1 | 12/2003 | Vigh |
| 2005/0009994 A1* | 1/2005 | Solomon ................ B01D 71/38 525/329.7 |
| 2010/0323573 A1 | 12/2010 | Chu et al. |
| 2013/0175218 A1* | 7/2013 | Chu .......................... C12H 3/02 210/640 |
| 2015/0076056 A1 | 3/2015 | Iyuke et al. |
| 2016/0367722 A1* | 12/2016 | Bumgardner ........... A61L 15/28 |

OTHER PUBLICATIONS

Ryu, K., et al., "Plasma protein adsorption to anion substituted poly (vinyl alcohol) membranes," Macromolecular Research, 2003, vol. 11, pp. 451-457.

International Preliminary Report on Patentability in Application No. PCT/AU2017/050361, dated Mar. 26, 2018.

Bhardwaj, et al., "A review of the development of a vehicle for localized and controlled drug delivery for implantable biosensors." *J Diabetes Sci Technol.*, 2(6):1016-27 (2008).

* cited by examiner

BIOCOMPATIBLE POLYMERIC MEMBRANES

RELATED APPLICATIONS

This application is a national stage filing under 35 U.S.C. 371 of International Application No. PCT/AU2017/050361, filed Apr. 21, 2017, which claims the benefit of U.S. Provisional Application No. 62/326,331, filed Apr. 22, 2016. The entire teachings of the above applications are incorporated herein by reference.

FIELD OF THE INVENTION

The present invention relates to polymeric membranes. In particular, the present invention relates to the use of polyvinyl alcohol membranes in electrophoresis.

The present application claims priority from U.S. Patent Application No. 62/326331, which is incorporated in its entirety herein by reference.

BACKGROUND OF THE INVENTION

Any discussion of the prior art throughout the specification should in no way be considered as an admission that such prior art is widely known or forms part of common general knowledge in the field.

Electrophoresis is the motion of dispersed particles relative to a fluid under the influence of an electric field. The combination of electrophoresis with a porous membrane, which allows the passage of macromolecules or cells of particular sizes and/or charges, enables the separation and/or purification of macromolecules or cells.

In electrophoretic separation of macromolecules or cells, a porous size exclusion membrane (separation membrane) is used to put into contact two liquids, between which the transfer of macromolecules or cells takes place under the influence of an electric field generated perpendicular to the separation membrane (Galier & Roux-de Balmann, *J. Membrane Sci.* 2004, 241: 79-87; Saxena et al., *Adv. Colloid Interface Sci.* 2009, 145: 1-22). Sample and harvest chambers are formed using two restriction membranes located on either side of a separation membrane (FIG. 1). The restriction membranes have very small pore sizes, which retain aqueous solutions with trans-membrane pressure but conduct current when used with an ionic buffer (Horvath et al., *Electrophoresis* 1994, 15 (1), 968-971).

Electrophoresis offers several advantages over convention separation techniques. In particular, greater separation resolution compared to conventional pressure-driven membrane filtration (due to the pH dependant electrophoretic mobility of macromolecules) and operation under lower shear conditions compared to chromatographic or ultrafiltration-based fractionation techniques, better preserving protein structure.

One such electrophoresis device is the Gradiflow apparatus, which utilises a polyacrylamide (PAm) separation membrane of controlled pore size to achieve size exclusion of macromolecules (Z. S. Horvath, G. L. Corthals, C. W. Wrigley, J. Margolis, Electrophoresis 1994, 15 (1), 968-971). The pore size of the separation membrane is controlled by varying the composition of the PAm reagent solution during membrane preparation. Feed (upstream) and product (downstream) chambers are formed using two restriction PAm membranes located on either side of a PAm separation membrane (FIG. 1). The restriction membrane has very small pore sizes, which retain aqueous solutions with trans-membrane pressure but conduct current when used with an ionic buffer.

However, PAm membranes have several disadvantages which limit commercial application:

Preparation of the PAm membranes requires stringent oxygen-free conditions, which is capital and labour-intensive to scale-up;

Fabrication of PAm membranes requires use of toxic acrylamide (Am) monomer, which has health and safety implications for manufacture. Additionally, residual Am monomer in the membranes may raise regulatory concern in applications targeting therapeutic administration of fractionated biomacromolecules;

PAm membranes are subject to membrane fouling.

Accordingly, there is a need for alternative membranes suitable for use in electrophoresis to separate macromolecules, wherein the membranes are easy and safe to manufacture, wherein the membranes do not contaminate macromolecules passing through the membrane or coming into contact with the membrane, and wherein the membranes have reduced membrane fouling.

It is an object of the present invention to overcome or ameliorate at least one of the disadvantages of the prior art, or to provide a useful alternative.

SUMMARY OF THE INVENTION

The present inventors have found that certain poly (vinyl alcohol) (PVA) membranes are suitable for use in electrophoresis.

In one aspect, the present invention relates to use of at least one polymeric membrane in the separation of one or more macromolecules and/or cells by electrophoresis, wherein the membrane comprises PVA.

In one embodiment, the membrane is a hydrogel.

In one embodiment, the membrane has a neutral net charge.

In one embodiment, the macromolecules are selected from the group consisting of proteins, peptides, DNA and RNA.

In another embodiment, the PVA has a molecular weight in the range of about 6 kDa to about 186 kDa, preferably about 20 kDa to about 100 kDa.

In another embodiment, the concentration of the PVA in the membrane in the range of about 5 to about 40% w/w, preferably about 5 to about 15% w/w.

In another embodiment, the membrane further comprises an additional polymer.

In another embodiment, the additional polymer is poly (ethylene glycol) (PEG) or poly(N-vinylpyrrolidone) (PVPON).

In another embodiment, the molecular weight of the additional polymer is in the range of about 1 kDa to about 60 kDa.

In another embodiment, the concentration of the additional polymer in the membrane is in the range of about 0.5 to about 3% w/w.

In another embodiment, the membrane is a restriction membrane.

In another embodiment, the restriction membrane has a molecular weight cut off (MWCO) of less than about 15 kDa.

In another embodiment, the restriction membrane has a MWCO of less than about 5 kDa.

In another embodiment, the restriction membrane has a shelf life of at least 8 months at 2-8° C.

In another embodiment, the restriction membrane is prepared by a casting and annealing method.

In another embodiment, the restriction membrane is prepared by a method comprises the steps of:
polymer solution preparation;
casting in appropriate casting unit;
drying of the membrane;
annealing at appropriate temperature in an oven; and
cooling and storage.

In another embodiment, the restriction membrane comprises a support substrate.

In another embodiment, the membrane is a porous size exclusion membrane (separation membrane).

In another embodiment, the separation membrane has a sponge-like structure, wherein the pores in the membrane are filled with water and create a torturous path for macromolecules and/or cells to migrate through.

In another embodiment, the separation membrane has a MWCO of at least 50 kDa.

In another embodiment, the separation membrane has a MWCO of about 200 kDa.

In another embodiment, the separation membrane has a MWCO of about 250 kDa.

In another embodiment, the separation membrane has a MWCO of about 1,000 kDa.

In another embodiment, the separation membrane has a pore size of less than about 10 μm.

In another embodiment, the separation membrane has a pore size of less than about 8 μm.

In another embodiment, the separation membrane has a pore size of less than about 5 μm.

In another embodiment, the separation membrane comprises a support substrate.

In another embodiment, the substrate is a non-woven material and hydrophilic in nature. Suitable materials include, but are not limited to, polyethylene terephthalate (PET), PVA, nylon, cellulose and cellulose derivatives.

In another embodiment, the separation membrane comprising a support substrate is prepared using a phase separation method.

In another embodiment, the separation membrane comprising a support substrate is prepared by a method comprises the steps of:
polymer solution preparation;
casting solution preparation incorporating non-solvent;
casting in appropriate casting unit;
non-solvent induced phase separation or evaporation;
annealing at appropriate temperature in an oven; and
cooling and storage.

In another embodiment, the substrate is a non-woven material and hydrophilic in nature. Suitable materials include, but are not limited to, polyethylene terephthalate (PET), PVA, nylon, cellulose and cellulose derivatives.

In another embodiment, the separation membrane does not comprise a support substrate.

In another embodiment, the separation membrane without a support substrate is prepared by non-solvent induced phase inversion method followed by post annealing.

In another embodiment, the separation membrane without a support substrate is prepared by a method comprising the steps of:
polymer solution preparation;
casting in appropriate casting unit/tank;
non-solvent induced phase inversion;
annealing at appropriate temperature in an oven; and
cooling and storage.

In another embodiment, the non-solvent is an alcohol.

In another embodiment, the non-solvent comprises ethanol and methanol.

In another embodiment, the non-solvent comprises isopropyl alcohol and acetone.

In another embodiment, the non-solvent comprises methanol.

In another embodiment, the non-solvent comprises acetone.

In another embodiment, the non-solvent comprises methanol and water.

In another embodiment, the non-solvent comprises acetone and water.

In another aspect, the present invention relates to a method for separating one or more macromolecules and/or cells from a first solution into a second solution, the method comprising the steps of:
separating the first and second solutions by means of a separation membrane comprising PVA, wherein the separation membrane has a preselected MWCO or pore size;
applying an electric field across the first and second solutions, wherein charged macromolecules and/or cells in the first solution that are smaller than the preselected MWCO or pore size pass through the separation membrane into the second solution.

In another aspect, the present invention relates to a method for separating one or more macromolecules and/or cells from a first solution into a second solution, the method comprising the steps of:
providing the first solution to a membrane stack comprising a separation membrane of the invention comprising PVA disposed between first and second restriction membranes comprising PVA, wherein the first solution lies between the first restriction membrane and the separation membrane and wherein the separation membrane has a preselected MWCO or pore size; and
applying an electrical field across the stack,
wherein charged macromolecules and/or cells in the first solution that are smaller than the preselected MWCO or pore size pass through the separation membrane into the second solution which lies between the separation membrane and the second restriction membrane.

In another aspect, the present invention relates to an electrophoresis system comprising:
a separation membrane comprising PVA disposed between two restriction membranes comprising PVA thereby defining first and second fluid chambers; and
means for providing an electric field passing from the first fluid chamber to the second fluid chamber through the separation membrane.

In another aspect, the present invention relates to a removable cartridge for use in an electrophoresis system, the cartridge comprising a separation membrane comprising PVA disposed between two restriction membranes comprising PVA thereby defining first and second fluid chambers, wherein the cartridge is adapted to be removably engaged in an electrophoresis system such that in use an electric field passes from the first fluid chamber to the second fluid chamber through the separation membrane.

In another embodiment, the restriction membranes allow passage of the electrical field, but do not allow passage of the first and second solutions.

In another embodiment, the present invention relates to a hydrogel membrane with neutral net charge, wherein the membrane comprises PVA and a support substrate.

In another embodiment, the hydrogel membrane with neutral net charge comprising PVA and a support substrate is a separation membrane and is prepared using a phase separation method.

In another embodiment, the phase separation method comprises the steps of:
  polymer solution preparation;
  casting solution preparation incorporating non-solvent;
  casting in appropriate casting unit;
  non-solvent induced phase separation or evaporation;
  annealing at appropriate temperature in an oven; and
  cooling and storage.

In the context of the present invention, the words "comprise", "comprising" and the like are to be construed in their inclusive, as opposed to their exclusive, sense, that is in the sense of "including, but not limited to".

As used herein, the term "separation membrane" means a porous size exclusion membrane.

As used herein the term "PAm" means polyacrylamide.

As used herein the term "PVA" means poly (vinyl alcohol).

As used herein the terms "MWO" or "molecular weight cut off" in relation to a membrane refer to the to the lowest molecular weight solute (in daltons) wherein at least 90% of the solute is retained by a membrane, or the approximate molecular weight of a molecule that is 90% retained by a membrane.

As used herein the term "macromolecule" means a molecule containing a very large number of atoms, commonly created by polymerization of smaller subunits (monomers). Examples of macromolecules include proteins, peptides, nucleic acids and synthetic polymers.

As used herein the term "pore size" in relation to a membrane refers to the average diameter of a macromolecule or cell that is retained by the membrane.

As used herein the term "membrane fouling" refers to a decrease in performance of a membrane caused by the deposition of a solution or particle on the external membrane surface, on the membrane pores, or within the membrane pores.

The terms 'preferred' and 'preferably' refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The recitation of a numerical range using endpoints includes all numbers subsumed within that range (e.g., 1 to 5 includes 1, 1.5, 2, 2.75, 3, 3.80, 4, 5, etc).

As used herein, the term "PVA membrane" means a membrane comprising PVA.

PREFERRED EMBODIMENT OF THE INVENTION

Figure 1:
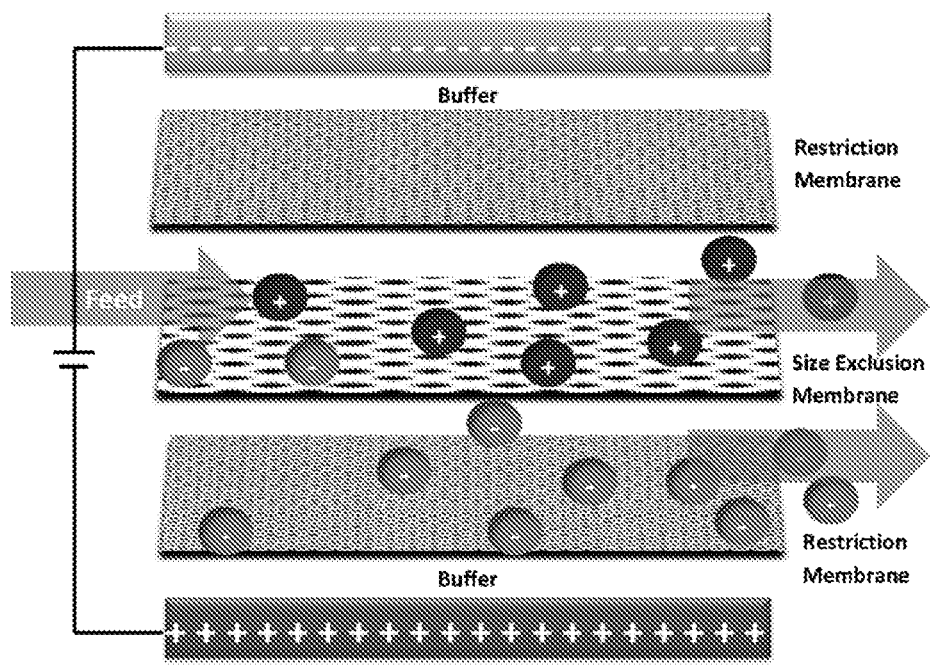
FIG. 1: Operating principle of the Gradiflow apparatus. Macromolecule fractionation is achieved either through differences in macromolecular charge or electrophoretic mobility; or membrane size exclusion due to differences in macromolecular radius.
Figure 2:
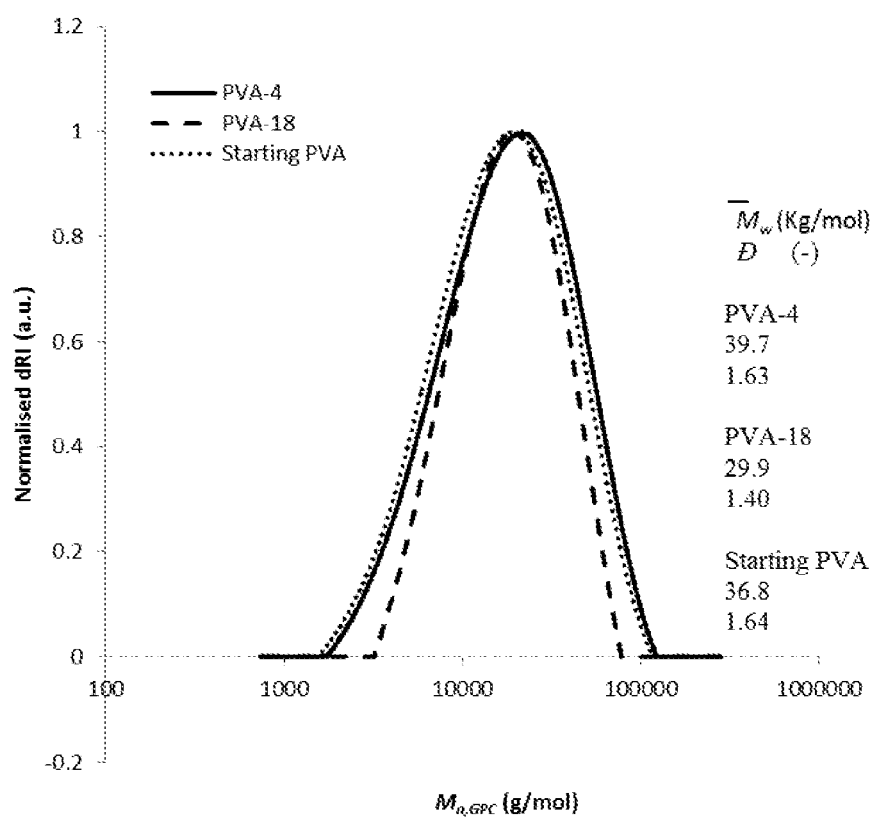
FIG. 2: GPC characterisation of PVA-4 and PVA-18 membranes; PVA membranes dissolved in hot $H_2O$ then subjected to GPC analysis. Sample of PVA starting material (22 kg/mol) shown for comparison. Mw reported relative to PEG standards.
Figure 3:
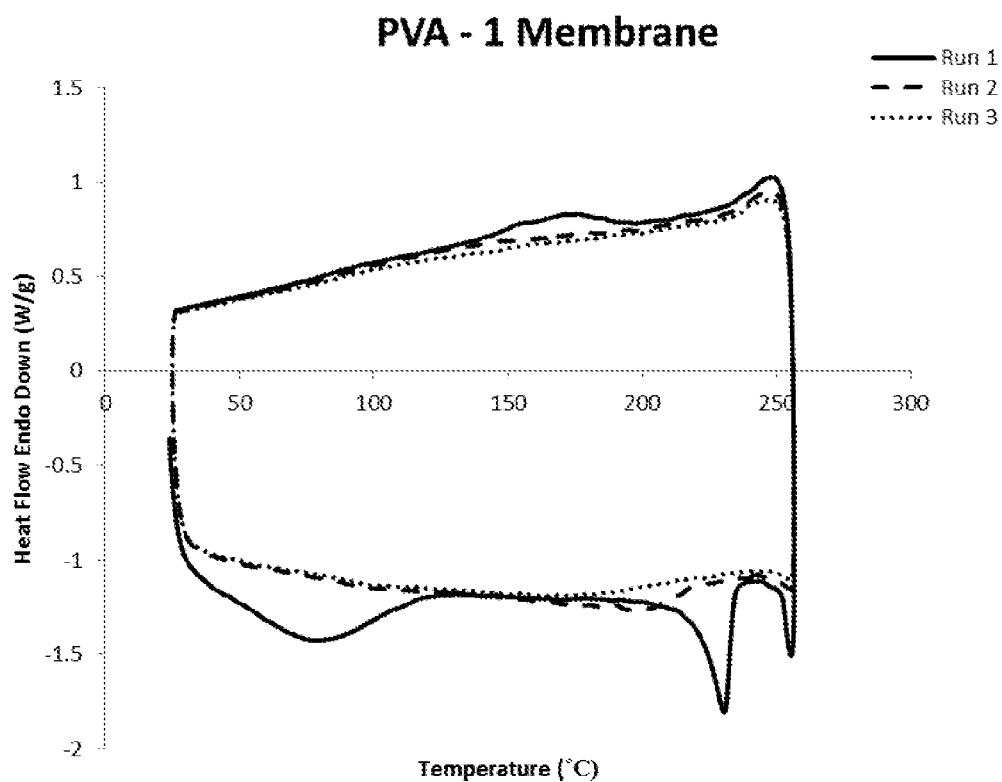
FIG. 3: DSC thermogram (25-260° C.) of PVA-1 membrane.
Figure 4:
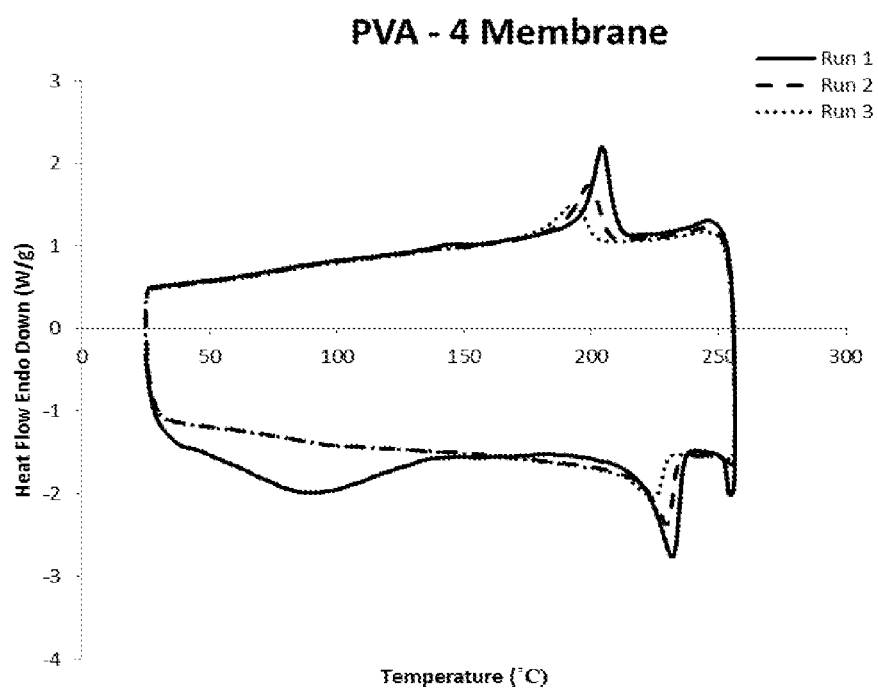
FIG. 4: DSC thermogram (25-260° C.) of PVA-4 membrane.
Figure 5:
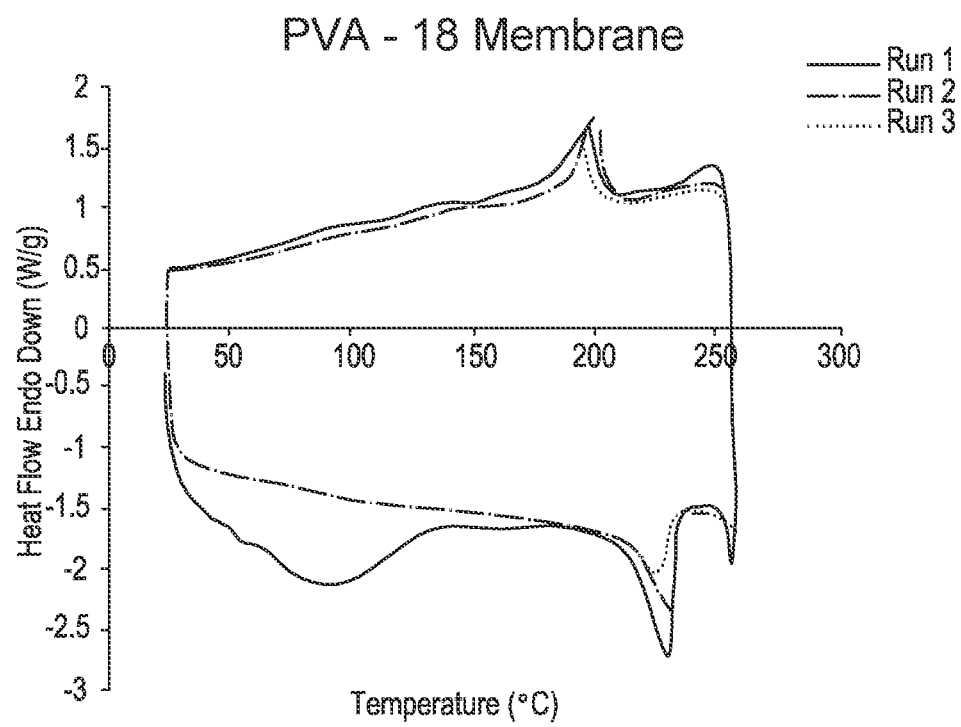
FIG. 5: DSC thermogram (25-260° C.) of PVA-18 membrane.
Figure 6:
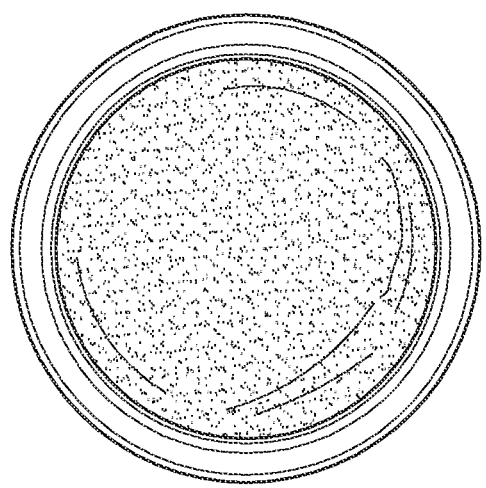
FIG. 6: Digital photograph of machined casting disc containing PVA membrane after phase inversion.

Although the invention has been described with reference to certain embodiments detailed herein, other embodiments can achieve the same or similar results. Variations and modifications of the invention will be obvious to those skilled in the art and the invention is intended to cover all such modifications and equivalents.

The present invention relates to the use of PVA separation and restriction membranes in electrophoresis for the separation of macromolecules and/or cells. The present invention also relates to methods for separating macromolecules and/or cells employing PVA membranes. The present invention further relates to electrophoresis systems comprising PVA membranes and removable cartridges for use in electrophoresis systems.

The use of PVA has several advantages for use in the separation of macromolecules and/or cells: PVA is hydrophilic which reduces membrane fouling by non-specific protein adsorption; it is biocompatible and neutral, aiding fabrication of membranes with low electroendosmosis (flow of bulk fluids through a membrane caused by an applied potential across membrane).

The PVA may have a molecular weight of about 10 kDa, about 20 kDa, about 30 kDa, about 40 kDa, about 50 kDa, about 60 kDa, about 70 kDa, about 80 kDa, about 90 kDa, about 100 kDa, about 110 kDa, about 120 kDa, about 130 kDa, about 140 kDa, about 150 kDa, about 160 kDa, about 170 kDa, or about 180 kDa.

The concentration of the PVA in the membrane may be about 5% w/w, about 10% w/w, about 15% w/w, about 20% w/w, about 25% w/w, about 30% w/w, about 35% w/w, or about 40% w/w.

The membrane may contain another polymer, such as poly(ethylene glycol) (PEG) or poly(N-vinylpyrrolidone) (PVPON), with a molecular weight of about 1 kDa, about 5 kDa, about 10 kDa, about 15 kDa, about 20 kDa, about 25 kDa, about 30 kDa, about 35 kDa, about 40 kDa, about 45 kDa, about 50 kDa, about 55 kDa, or about 60 kDa. The concentration of the additional polymer in the membrane may be about 0.5% w/w, about 1% w/w, about 1.5% w/w, about 2% w/w, about 2.5% w/w, or about 3% w/w.

PVA restriction membranes were prepared by casting and annealing, and characterised by a combination of techniques. These analyses revealed the predominant stabilising mechanism in the restriction membranes was non-covalent cross-linking due to the formation of crystalline domains.

Stability studies carried out on PVA restriction membranes and PAm restriction membranes (control) show that the PVA restriction membranes have a shelf life of at least 8 months at 2-8° C. In other embodiments, the shelf life at 2-8° C. is at least 9 months, at least 10 months, at least 11 months, at least 12 months, at least 13 months, at least 14 months, at least 15 months, at least 15 months, at least 16 months, at least 17 months, at least 18 months, at least 19 months, at least 20 months, at least 21 months, at least 22 months, at least 23 months, at least 24 months, at least 3 years, at least 4 years, or at least 5 years. In other embodiments, the PVA membranes have a shelf life of at least 8 months at 2° C., at 3° C., at 4° C., at 5° C., at 6° C., at 7° C., at 8° C., at 9° C., at 10° C., at 11° C., at 12° C., at 13° C., at 14° C., at 15° C., at 16° C., at 17° C., at 18° C., at 19° C., at 20° C., at 21° C., at 22° C., at 23° C., at 24° C., at 25° C., at 26° C., at 27° C., at 28° C., at 29° C., at 30° C., at 31° C., at 32° C., at 33° C., at 34° C., at 35° C., at 36° C., at 37° C., at 38° C., at 39° C., or at 40° C.

The MWCO of the restriction membrane may be about 1 kDA, about 2 kDA, about 3 kDA, about 4 kDA, about 5 kDA, about 6 kDA, about 7 kDA, about 8 kDA, about 9 kDA, about 10 kDA, about 11 kDA, about 12 kDA, about 13 kDA, about 14 kDA, or about 15 kDA.

PVA separation membranes without support substrates were prepared by a combination of casting and non-solvent induced phase inversion to generate a porous structure, followed by post annealing. This technique has numerous advantages with regard to future scale-up including: no charge residues on the membranes, existing widespread application in the membrane industry; and the experimental ease of the process compared to PAm membrane fabrication. The influence of a range of experimental parameters upon the pore size and pore morphology was studied using scanning electron microscopy (SEM). Variation of these parameters is known to modulate the kinetics of the phase inversion process, which has a direct influence on membrane pore size. Using a combination of alcoholic non-solvents (ethanol and methanol), PVA membranes with the desired sponge-like morphology and pore sizes ranging from 2-5 μm down to 100-300 nm could be prepared. The membranes show promising results for macromolecule fractionation such as blood plasma fractionation to separate valuable proteins such as Albumin and IgG. The casting solution is prepared in water (solvent), then casted and emerged in organic solvents (non-solvent) to invert the liquid phase of PVA to the solid phase while rearranging physically to create porous structure.

PVA separation membranes with support substrates were prepared by combination of casting solution preparation involving non-solvents, phase separation or evaporation to achieve desired pore size. The casting solution preparation using non-solvents reduces surface damage of the membranes. This also aids the manufacturing process by reducing bubbles and the fast wetting of the substrates during casting, which should be a great advantage to scale up the membrane manufacturing process compared with the scaling up of the PAm membrane manufacturing process. In preparation of membranes with substrates, the casting solution is prepared incorporating non-solvents. This provides a homogeneous mixture of PVA in water (solvent) and organic solvent (non-solvent) before a critical concentration of the non-solvent is reached (PVA precipitates out). The mechanism of phase separation in this method shows better control on the pore size. This method of phase separation which involves making PVA casting solution with non-solvent (organic solvents) has not been previously reported. The membranes may be cast into a machined die by pouring the casting solution over the support substrate.

The MWCO of the separation membrane may be about 50 kDA, about 100 kDA, about 150 kDA, about 200 kDA, about 250 kDA, about 300 kDA, about 350 kDA, about 400 kDA, about 450 kDA, about 500 kDA, about 550 kDA, about 600 kDA, about 650 kDA, about 700 kDA, about 750 kDA, about 800 kDA, about 850 kDA, about 900 kDA, about 950 kDA, or about 100 kDa.

The pore size of the separation membrane may be about 0.1 μm, about 0.2 μm, about 0.3 μm, about 0.4 μm, about 0.5 μm, about 0.6 μm, about 0.7 μm, about 0.8 μm, about 0.9 μm, about 1 μm, about 2 μm, about 3 μm, about 4 μm, about 5 μm, about 6 μm, about 7 μm, about 8 μm, about 9 μm, about 10 μm.

Within the restriction membrane, the PVA forms crystalline domains during annealing which serves as physical cross linking to create porous structure. For the separation membranes the pores are formed also due the physical rearrangements (physical cross linking) of the PVA polymer itself while precipitating from its liquid phase to the solid phase in presence of water and organic solvent (solvent and non-solvent).

The purpose of the support substrate is too provide the sufficient mechanical strength required to withstand any transmembrane or feed pressure during the electrophoresis over the time of separation process which could be six hours or longer. Both PVA restriction and separation membranes may have support substrates.

A membrane-based electrophoresis apparatus typically includes a cartridge which houses a number of membranes forming at least two chambers, cathode and anode in respective electrode chambers connected to a suitable power supply, reservoirs for samples, buffers and electrolytes, pumps for passing samples, buffers and electrolytes, and cooling means to maintain samples, buffers and electrolytes at a required temperature during electrophoresis. The cartridge contains at least three substantially planar membranes disposed and spaced relative to each other to form two chambers through which sample or solvent can be passed. A separation membrane is disposed between two restriction membranes. When the cartridge is installed in the apparatus, the restriction membranes are located adjacent to an electrode. The cartridge is described in AU 738361. Descriptions of membrane-based electrophoresis can be found in U.S.

Pat. Nos. 5,039,386 and 5,650,055. An apparatus particularly suitable for use in isoelectric separation applications can be found in WO 02/24314.

One electrophoresis apparatus suitable for use in the present invention comprises:
(a) a first electrolyte chamber;
(b) a second electrolyte chamber,
(c) a first sample chamber disposed between the first electrolyte chamber and the second electrolyte chamber;
(d) a second sample chamber disposed adjacent to the first sample chamber disposed and between the first electrolyte chamber and the second electrolyte chamber;
(e) a separation membrane disposed between the first sample chamber and the second sample chamber, the separation membrane preventing substantial convective mixing of contents of the first and second sample chambers;
(f) a first restriction membrane disposed between the first electrolyte chamber and the first sample chamber, the first restriction membrane preventing substantial convective mixing of contents of the first electrolyte chamber and the first sample chamber;
(g) a second restriction membrane disposed between the second sample chamber and the second electrolyte chamber, the second restriction membrane preventing substantial convective mixing of contents of the second electrolyte chamber and the second sample chamber; and
(h) electrodes disposed in the first and second electrolyte chambers.

The electrophoresis apparatus may further comprise one or more of:
(i) an electrolyte reservoir;
(j) a first sample reservoir and a second sample reservoir;
(k) means for supplying electrolyte from the electrolyte reservoir to the first and second electrolyte chambers; and
(l) means for supplying sample or liquid from at least the first sample reservoir to the first sample chamber, or from the second sample reservoir to the second sample chamber.

The apparatus may further comprise:
(m) a first electrolyte reservoir and a second electrolyte reservoir; and
(n) means for supplying electrolyte from the first electrolyte reservoir to the first electrolyte chamber and electrolyte from second electrolyte reservoir to the second electrolyte chamber.

The apparatus may further comprise one or more of:
means for circulating electrolyte from the electrolyte reservoir(s) through the electrolyte chambers forming electrolyte streams in the electrolyte chambers; and
means for circulating contents from each of the first and second sample reservoirs through the respective first and second sample chambers forming first and second sample streams in the respective sample chambers;
means for removing and replacing sample in the first or second sample reservoirs; and
means to maintain temperature of electrolyte and sample solutions.

The present invention is further described by the following non-limiting examples.

EXAMPLES

Example 1

Materials and Methods

Chemicals—$PVA_{89k}$ (89-98 kg/mol), $PVA_{22k}$ (22 kg/mol), $PEG_{8k}$ (6 kg/mol), $PEG_{2k}$ (2 kg/mol) and $PVPON_{10k}$, $PVPON_{40k}$, $PVPON_{50k}$ (10, 40 and 55 kg/mol respectively) were obtained from Sigma Aldrich at the highest purity grades available.

Membrane substrate—Polyethyleneterapthalate (PET) fibre sheets were used as a substrate for casting the membranes. PET fibre sheets are FDA compliant for use in various biological assays and separation processes. The substrates are engineered for excellent fluid transfer properties, have high thermal bonding properties for use in higher temperature applications. Good thermal bonding properties maintain part integrity during normal transportation, storage, and use. The substrates come in sheets or rolls and were purchased from Shangshai Bolting cloth manufacturing, China.

Example 2

PVA Restriction Membrane Preparation and Characterisation

To prepare a PVA stock solution, a known quantity of high-purity water was added to a round bottom flask. The flask was placed in a thermostatic oil bath (90° C.) and stirred under reflux. A known mass of PVA was added until the desired concentration (% w/w) was achieved. The slurry was stirred at 90° C. until no undissolved gel was observed, forming a viscous solution. Following, the solution was stirred an additional 30 min at reflux to ensure complete dissolution of PVA. The solution was cooled slowly to room temperature with gentle mixing, then weighed. If necessary, high-purity water was then added to return the net mass to the starting mass to produce the desired concentration (% w/w). Following, the solution was gently stirred at room temperature for 30 minutes, and then stood overnight without stirring to remove entrained bubbles.

Stock solutions of PEG and PVPON in water were prepared by dissolving appropriate PEG and PVPON in water to the desired concentration (% w/w).

PVA restriction membranes were prepared by casting and annealing method. The membrane casting solutions were prepared by mixing an appropriate mass of PVA solution, additive solution (PEG or PVPON, varied $M_w$) and high-purity $H_2O$. The solutions were stirred for a minimum of 30 minutes to ensure all components were well mixed, then stood for 30 minutes at room temperature to allow any entrained bubbles to be collected. The membranes were cast into a membrane casting tank comprising two layers of PET substrates. Following air-drying, the membranes were annealed at 110° C. for 1 hr, then swollen for 48 hours in high-purity $H_2O$ before analysis. The membrane formulations details are listed in Table 1.

TABLE 1

| | Formulations of PVA restriction membranes | | |
|---|---|---|---|
| Batch No | PVA (% w/w) | PEG (% w/w) | Annealing at 110° C. |
| PVA-1 | $PVA_{89k}$ (10%) | 0% | Yes |
| PVA-4 | $PVA_{22k}$ (15%) | 0% | Yes |
| PVA-18 | $PVA_{22k}$ (14%) | $PEG_{8k}$ (1%) | Yes |

To investigate PVA cross-linking (leading to $M_w$ increase), PVA restriction membranes were subjected to gel permeation chromatography (GPC) analysis.

To determine the presence of crystallinity in the PVA membrane samples, dried samples were subjected to differential scanning calorimetry (DSC) analysis. The thermal program consisted of an initial isothermal step at 25° C. for 3 min, followed by heating/cooling cycle from 25-260° C. at 10° C./min, then 260-25° C. at 10° C./min. Two more heating and cooling cycles were then repeated.

GPC analysis upon the material released by dissolving PVA-4 and PVA-18 membranes in hot water revealed no significant shift in $M_w$ compared to the starting material PVA (22 kg/mol, $M_w$ provided by manufacturer). This suggests that no significant covalent cross-linking, due to heat-induced chain scission, took placed during the annealing process. Although it is possible that insoluble networks could have been generated during annealing, which would not be detectable by GPC, the low temperature (110° C.) using during annealing is not likely to result in significant chain scission and cross-linking.

DSC analysis of PVA-1, PVA-4 and PVA-18 membranes indicated the presence of crystallinity in all the samples, as evidenced by the large endothermic peak centred around 230° C., attributed to melting of crystalline PVA domains. In combination with the GPC analysis, these results strongly suggest that formation of crystalline domains following annealing is the predominant mechanism cross-linking the membranes. These observations agree with literature findings demonstrating cross-linking by crystallisation at low temperature (<160° C.). The absence of an exothermic crystallization peak for the PVA-1 sample is likely due to the slower crystallization kinetics of 89 kg/mol PVA compared to 22 kg/mol; this effect is ascribed to the higher mobility of the low $M_w$ PVA chains compared to high $M_w$ chains.

Example 3

PVA Separation Membrane (Without Support Substrate) Preparation and Characterisation PVA, PEG and PVPON stock solutions were prepared as described for restriction PVA membranes.

PVA separation membranes were prepared by non-solvent induced phase inversion. In the first instance, the membranes with varying pore sizes were prepared without any support substrates for ease of characterisation. The membrane casting solutions were prepared by mixing an appropriate mass of PVA solution (89 kg/mol), additive solution (PEG or PVPON, varied Mw) and high-purity $H_2O$. The solutions were stirred for a minimum of 30 minutes to ensure all components were well mixed, then stood for 30 minutes at room temperature to allow any entrained bubbles to be collected. The membranes were cast into machined wells formed in stainless steel discs (internal diameter=55 mm, well depth=1 mm), air-dried for 5 minutes, and then immersed in a non-solvent coagulation bath (200 mL).

The composition of the non-solvent bath was varied by altering the volume ratios of $H_2O$, methanol (MeOH) and ethanol (EtOH). The membranes were held in the coagulation bath for a minimum for 60 minutes. To reduce membrane shrinkage and pore collapse upon drying, after coagulation, the membranes were immersed in an acetone bath (100 mL) for 15 minutes, then removed and placed on a glass plates and air-dried. Following air-drying, the membranes were annealed at 110° C. for 1 hr, then swollen for 48 hours in 2×100 mL portions of high-purity $H_2O$ before analysis. The PVA separation membrane formulations with PEG additives are shown in Table 2. Strength of hydrated membranes fabricated from high molecular weight PVA (89-98 kg/mol) is very good; can be manipulated easily with tweezers, can be stretched.

TABLE 2

Formulation table for PVA-64, PVA-66 and PVA-67 separation membranes

| Batch No | PVA (% w/w) | Additive (% w/w) | Phase Inversion | Annealing at 110° C. |
|---|---|---|---|---|
| PVA-64 | $PVA_{89k}$ (11.0%) | $PEG_{2k}$ (0.91%) | 64:21:15 v/v EtOH/MeOH/$H_2O$, 90 min | Yes |
| PVA-66 | $PVA_{89k}$ (11.0%) | $PEG_{2k}$ (0.91%) | 21:64:15 v/v EtOH/MeOH/$H_2O$, 90 min | Yes |
| PVA-67 | $PVA_{89k}$ (11.0%) | $PEG_{2k}$ (0.91%) | 85:15 v/v MeOH/$H_2O$, 90 min | Yes |

PVA separation membrane formulations with PVPON additive are shown in Table 3.

TABLE 3

Formulation table for PVA-80, PVA-81 PVA-83 separation membranes

| Batch No | PVA (% w/w) | Additive (% w/w) | Phase Inversion | Annealing at 110° C. |
|---|---|---|---|---|
| PVA-80 | $PVA_{89k}$ (11.8%) | $PVPON_{10k}$ (0.91%) | 85:15 v/v MeOH/$H_2O$, 90 min | Yes |
| PVA-81 | $PVA_{89k}$ (11.8%) | $PVPON_{10k}$ (0.91%) | 6.5:78.5:15 v/v EtOH/MeOH/$H_2O$, 90 min | Yes |
| PVA-83 | $PVA_{89k}$ (11.8%) | $PVPON_{10k}$ (0.91%) | 19.5/65.5:15 v/v MeOH/$H_2O$, 90 min | Yes |

The membranes were characterised using SEM analysis. The SEM imaging was performed in low vacuum (0.5-0.6 mbar $H_2O$ pressure) using an FEI Quanta environmental scanning electron microscope. Samples were imaged without a gold coating to prevent occlusion of the pores due to the gold layer.

Figure 7:
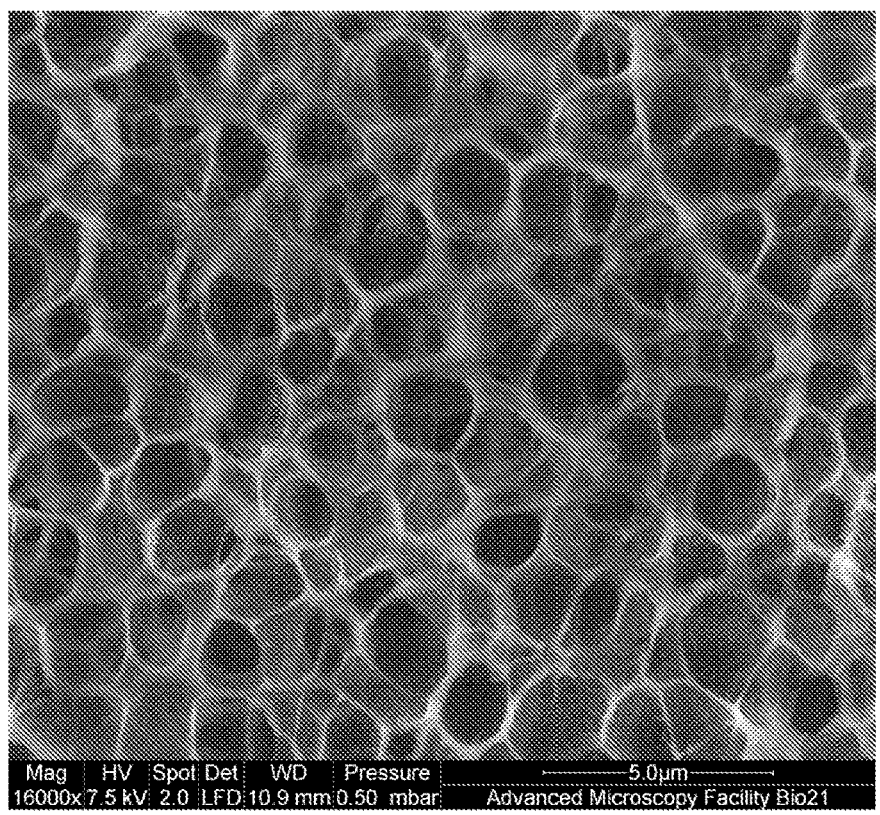
FIG. 7: SEM micrograph of UoM-PVA-64 (11.0% w/w $PVA_{89k}$) membrane cross-section prepared by phase inversion in 64:21:15 v/v EtOH/MeOH/$H_2O$ showing pore size in large pore size region.
Figure 8:
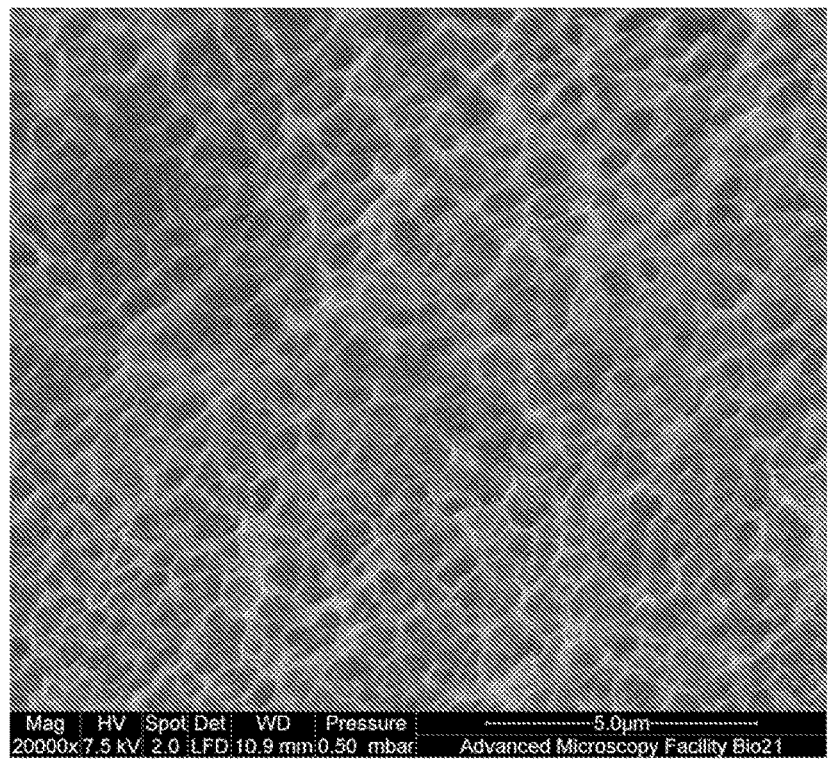
FIG. 8: SEM micrograph of UoM-PVA-66 (11.0% w/w $PVA_{89k}$) cross-section prepared by phase inversion in 21:64:15 v/v EtOH/MeOH/$H_2O$ showing pore size distribution.
Figure 9:
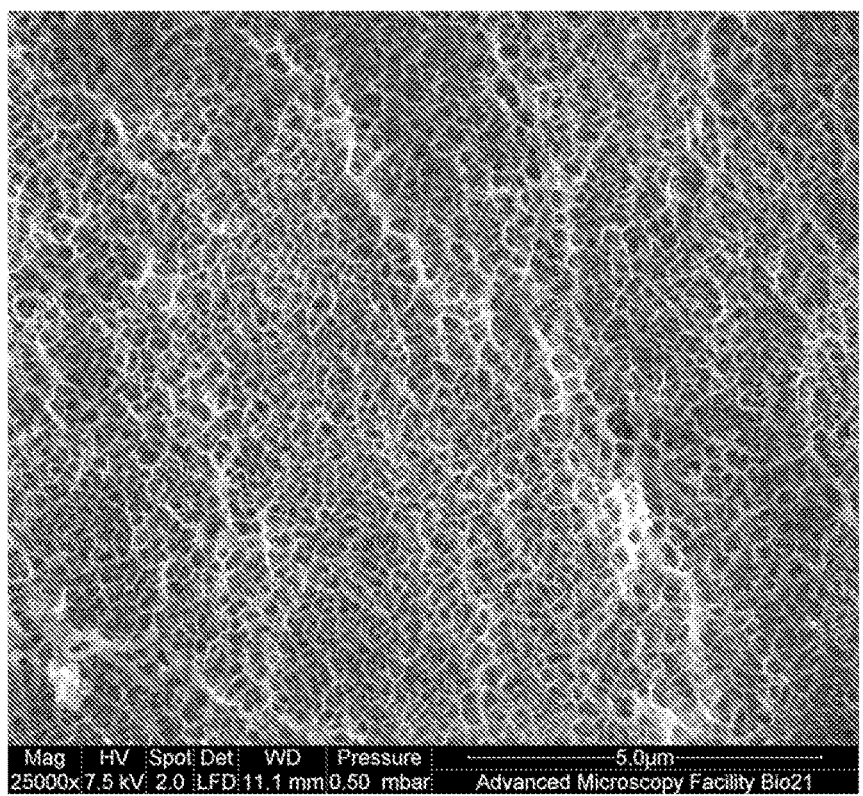
FIG. 9: SEM micrograph of UoM-PVA-67 (11.0% w/w $PVA_{89k}$) membrane cross-section prepared by phase inversion in 85:15 v/v MeOH/$H_2O$ showing pore size distribution.

The SEM images for PVA-64, PVA-66 and PVA-67 are shown in FIGS. 7, 8 and 9 respectively. The SEM results show sponge like porous structure has formed during phase inversion process. Variation of non-solvent composition (MeOH/EtOH ratio) potentially promising method to tune pore size.

Figure 10:
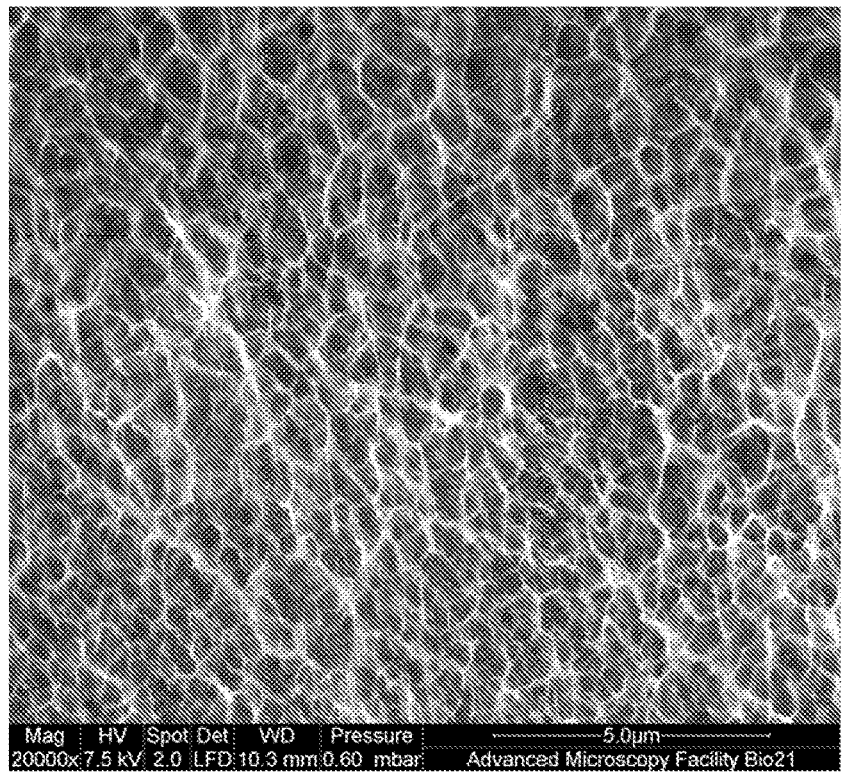
FIG. 10: SEM micrograph of UoM-PVA-80 (11.8% w/w $PVA_{89k}$) membrane cross-section prepared by phase inversion in 85:15 v/v MeOH/$H_2O$ pore size distribution toward air side of membrane.
Figure 11:
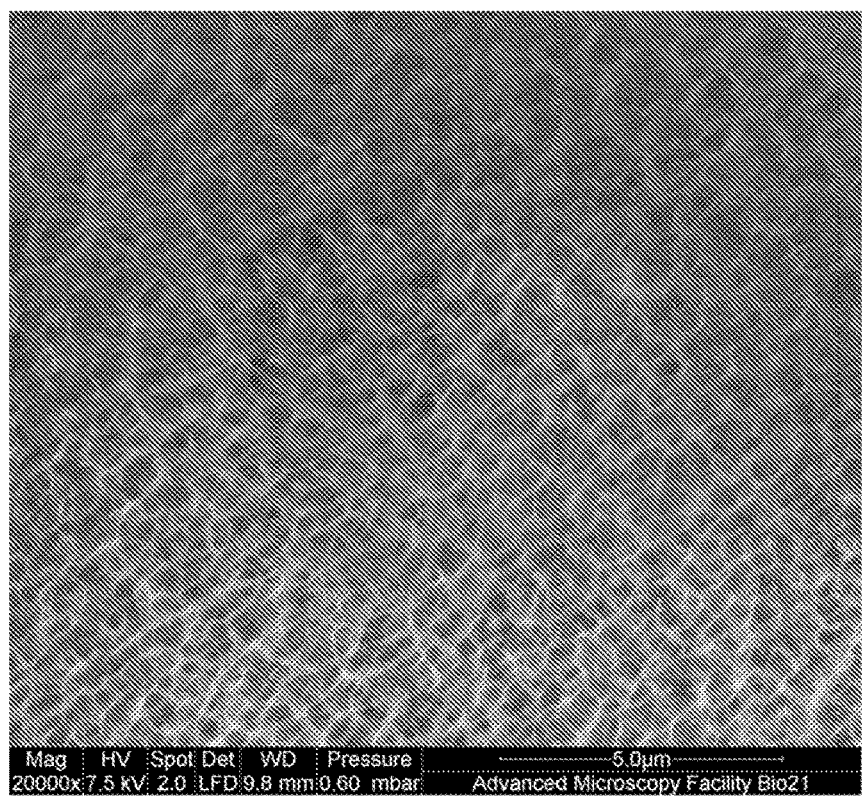
FIG. 11: SEM micrograph of UoM-PVA-81 (11.8% w/w $PVA_{89k}$) membrane cross-section prepared by phase inversion in 6.5:78.5:15 v/v EtOH/MeOH/$H_2O$ pore size distribution toward die side of membrane.
Figure 12:
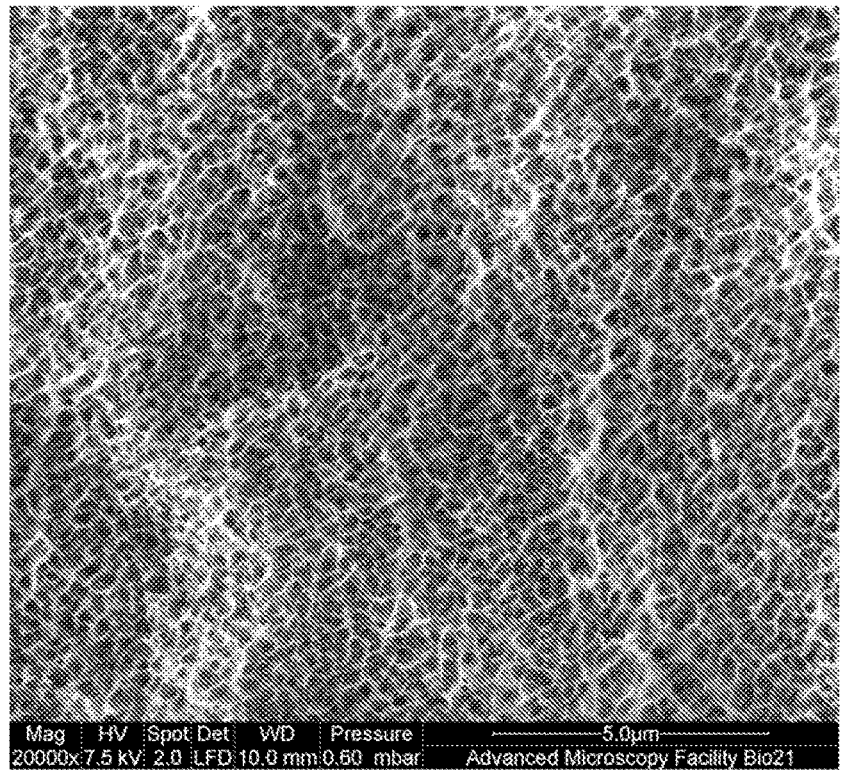
FIG. 12: SEM micrograph of UoM-PVA-83 (11.8% w/w $PVA_{89k}$) membrane cross-section prepared by phase inversion in 19.5:65.5.5:15 v/v EtOH/MeOH/$H_2O$ pore size distribution toward air side of membrane.

The SEM images for PVA-80, PVA-81 and PVA-82 are shown in FIGS. 10, 11 and 12 respectively. The SEM results show sponge like porous structure has formed during phase inversion process. However, asymmetric pore size distribution between air side and die side of membrane is more pronounced using PVPON additive than PEG additive.

Example 4

Figure 13:
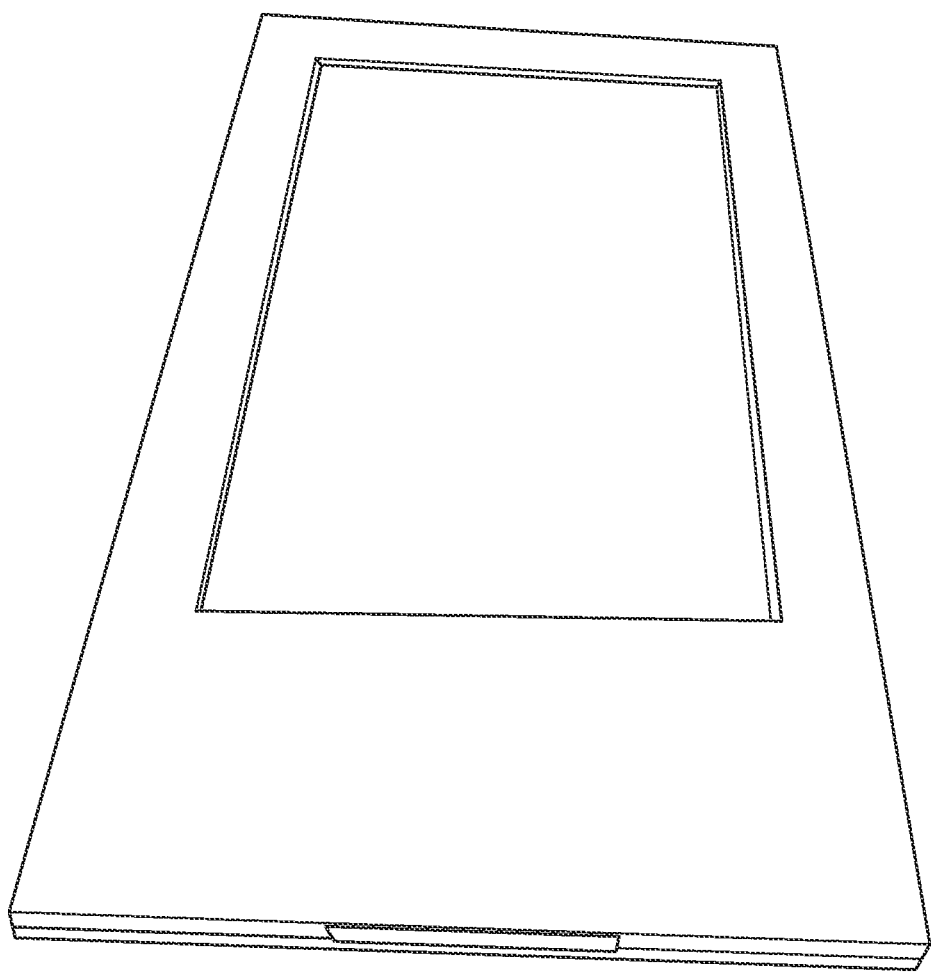
FIG. 13: A4-size membrane casting unit.

PVA Separation Membrane (With Support Substrate) Preparation and Characterisation The casting solutions for the PVA separation membranes with support substrates were prepared by mixing an appropriate mass of PVA solution (89 kg/mol), additive solution (PEG), high-purity $H_2O$ and non-solvents in different ratios. The PVA and PEG solutions were first prepared in water by stirring for a minimum of 30 minutes before adding the non-solvent to ensure all components were well mixed, then stood for 30 minutes at room temperature to allow any entrained bubbles to be collected. The non-solvents, ethanol or acetone mixed with water, were then added in different ratios and stirred for 5 minutes, then stood for another 10 minutes to remove any entrained bubbles. The critical concentration of the non-solvent mix above which PVA precipitates out was achieved at 80:20 for Ethanol:$H_2O$, and at 50:50 for Acetone:$H_2O$. The membranes were cast into a machined die (internal dimension=292 mm×187 mm×2 mm) (FIG. 13) by pouring the casting solution over a PET substrate.

To reduce membrane shrinkage and pore collapse upon drying, after coagulation or semi-evaporation, the membranes were immersed in an acetone/ethanol bath (100 mL) for 15 minutes to 12 hours, then removed, placed on a glass plate and air-dried. Following air-drying, the membranes were annealed at 100° C. for 20 minutes, then swollen for 48 hours in 2×100 mL portions of high-purity $H_2O$ before analysis. The PVA separation membrane formulations are shown in Table 4. Polymer solution preparation with non-solvents has significantly improved the substrate wetting and bubble removal during casting, which facilitates scaling up the membrane manufacturing process. Membranes cast without non-solvent mixing had membrane damage during phase inversion in the coagulation bath, and pore size could not be opened as expected. All membranes were in A4 size.

TABLE 4

Formulation table for separation membranes

| Batch | PVA (% w/w) | Additive (% w/w) | Non-solvent ratio | Annealing at 100° C. |
|---|---|---|---|---|
| SPVA-1 | $PVA_{89k}$ (11.0%) | $PEG_{6k}$ (0.8%) | 80:20 v/v EtOH/$H_2O$, Mixing at 40:60 polymer/non-solvent ratio Acetone treated after air drying | Yes |
| SPVA-2 | $PVA_{89k}$ (11.0%) | $PEG_{6k}$ (0.8%) | 75:15 v/v EtOH/$H_2O$, Mixing at 15:75 polymer/non-solvent ratio | Yes |
| SPVA-3 | $PVA_{89k}$ (11.0%) | $PEG_{6k}$ (0.8%) | 50:50 v/v Acetone/$H_2O$, Mixing at 15:75 polymer/non-solvent ratio | Yes |
| SPVA-4 | $PVA_{89k}$ (11.0%) | $PEG_{6k}$ (0.8%) | 80:20 v/v EtOH/$H_2O$, Mixing at 50:50 polymer/non-solvent ratio Acetone treated after air drying | Yes |
| SPVA-5 | $PVA_{89k}$ (11.0%) | $PEG_{6k}$ (0.8%) | 80:20 v/v EtOH/$H_2O$, Mixing at 40:60 polymer/non-solvent ratio Ethanol treated (2-8° C.)after air drying | Yes |
| SPVA-6 | $PVA_{89k}$ (11.0%) | $PEG_{6k}$ (0.8%) | 50:50 v/v EtOH/$H_2O$, Mixing at 50:50 polymer/non-solvent ratio Ethanol treated (2-8° C.)after air drying | Yes |

Example 5

Functional Testing of Restriction Membranes

Figure 14:
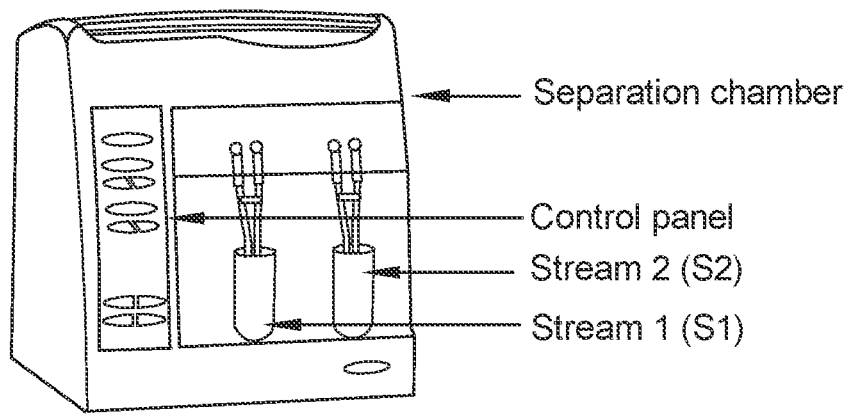
FIG. 14: BF400 electrophoresis separation apparatus.

The Gradiflow™ BF 400 (Gradipore) electrophoresis apparatus was used to carry out the functional test to determine the pore size of a membrane and its suitability for plasma protein separation. A schematic diagram of BF400 electrophoresis apparatus is shown in FIG. 14. With a processing volume of between 5 and 50 mL, it is a versatile system capable of processing samples from a diverse range of biological complex. The control panel has time setting key, voltage key, buffer pump start key, stream pump start key, cover indicator, electrical reverse key and start and stop key. The machine has a fixed stream pump and buffer pump, stream pump gives a fixed stream flow rate to both stream 1 and 2 at 20 ml/min, the buffer pump circle the buffer at 2 L/min.

Figure 15:
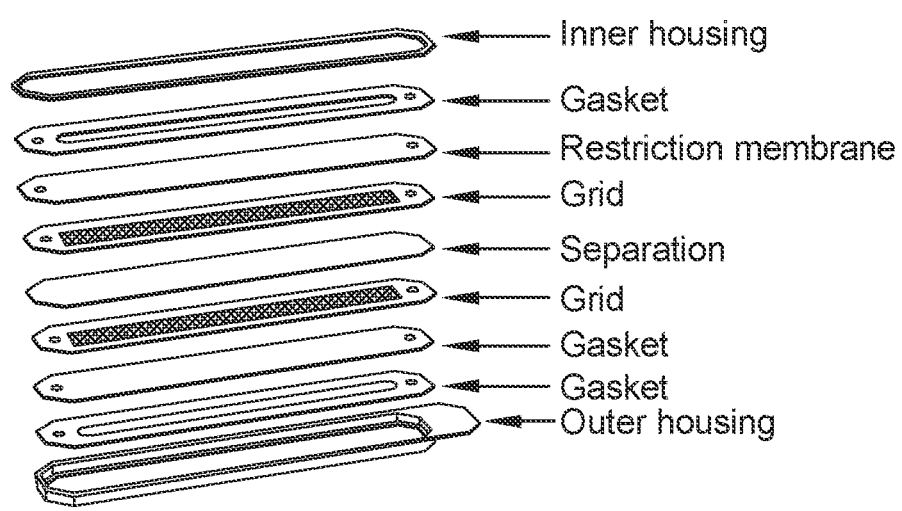
FIG. 15: Cartridge assembly for BF400 apparatus.

A BF400 cartridge was assembled according to FIG. 15. The membranes are cut into the required size using appropriate die and assembled in the cartridges.

The following example shows functional testing of PVA restriction membranes in comparison to PAm restriction membranes. The test was performed based on the separation of bovine insulin using the BF400 electrophoresis apparatus.

Bovine insulin 5 kDa was obtained from Sigma Aldrich, A 0.5 mg/mL stock solution of insulin was prepared in Tris-Hepes buffer (pH: 8.4). A BF400 membrane cartridge comprising two PAm restriction membranes (which have been confirmed as having 5-kDa or smaller pore sizes) and a restriction PVA membrane (PVA-1, PVA-4 or PVA18 from Example 2) sandwiched between the PAm restriction membranes (i.e., in the separation membrane position) was used in the separation unit. Tris-Hepes buffer was circulated in the buffer tank and kept cold with a chiller connected to the unit. A leak test was performed for 10 minutes by placing 10 mL of Tris-Hepes buffer in both stream 1 (51) and stream 2 (S2). The functional tests were carried out using an electric potential of 150 V with the positive electrode configured at S2, was placed across the membrane sandwich to perform the electrophoresis. The protein solution was placed in S1 and Tris-Hepes buffer in S2. The samples in S1 and S2 were harvested after 30 minutes and the protein concentration in both S1 and S2 was measured to calculate percentage transfer of the protein. The functional test for the control was performed with the same conditions but with the PVA restriction membrane replaced with a PAm restriction membrane.

The functional tests results are shown in Table 5. The results show that the performance of PVA restriction membranes is comparable to PAm restriction membranes (control), and that PAm restriction membranes can be replaced with biocompatible PVA restriction membranes for plasma fractionation application.

TABLE 5

Functional test results for PVA restriction membranes in comparison to PAm restriction membranes (EEO = electroendosmosis)

| Batch No | Target Insulin transfer | Actual Insulin transfer | Target EEO | Actual EEO | Pass/fail |
|---|---|---|---|---|---|
| PVA-1 | <2% | 0% | <0.8 | 0.06 | Pass |
| PVA-4 | <2% | 0.6% | <0.8 | 0 | Pass |
| PVA-18 | <2% | 1.7% | <0.8 | 0.6 | Pass |
| Control | <2% | 0.4% | <0.8 | 0.7 | Pass |

Example 6

Functional Testing of Separation Membranes

The following example shows functional testing of PVA separation membrane performance compared to PAm separation membrane performance in relation to plasma protein separation. The test was performed based on the separation of bovine immunoglobulin G (IgG) using the BF400 electrophoresis apparatus.

Bovine IgG 150 kDa obtained from Sigma Aldrich, A 2 mg/mL stock solution of IgG was prepared in Tris-Hepes buffer (pH: 8.4). A BF400 membrane cartridge was prepared comprising a PVA separation membrane sandwiched between two PAm restriction membranes. Tris-Hepes buffer was circulated in the buffer tank and kept cold with a chiller connected to the unit. A leak test was performed for 10 minutes by placing 10 mL of Tris-Hepes buffer in both stream 1 (S1) and stream 2 (S2). The functional tests were carried out using an electric potential of 200 V with the positive electrode configured at S2. The protein solution was placed in S1 and Tris-Hepes buffer in S2. The samples in S1 and S2 were harvested after 30 minutes and the protein concentration in both S1 and S2 was measured to calculate percentage transfer of the protein. The functional test for the control was performed at the same conditions but with the PVA separation membrane replaced with a PAm separation membrane.

The functional tests results are shown in Table 6. The results show that the PVA separation membrane performance is comparable or better to the PAm separation membrane performance, and that PAm separation membranes can be replaced with biocompatible PVA separation membranes for plasma fractionation. The overall protein recovery is greater for PVA membranes compared to PAm membranes, which may be attributed to the reduced membrane fouling of PVA membranes.

electrode configured at S2. The protein solution was placed in S1 (sample chamber) and Tris-Borate buffer in S2 (harvest chamber). The samples in S1 and S2 were harvested after 30 minutes. The functional tests were also performed by placing two PCT membranes in the restriction position and the PAm restriction membrane in the separation position sandwiched between two PCT membranes. The same was repeated for the commercial membrane 2 (PES).

The results show that for both PES and PCT, at 200V, there was high electro-endosmosis when the commercial membrane was used in the separation position. It was less as the voltage was lowered, at 20 V, still 20% solution of the harvest chamber (S2) was migrated to the sample chamber (S1). It could be attributed to the bulk water flowing in the sample chamber (S1 when voltage was applied and protein tends to migrate towards the harvest chamber (S2). These could be because protein might have adsorbed on the membrane surface and cannot move causing the water flowing in the opposite direction. It could also be due the high flux related the high permeability of the flat sheet membranes compared to the hydrogel membranes. When the commercial membranes were placed in the restriction position, there was no solvent loss in any chamber; however some solvent overflowing in both chambers and current dropping suggests may be solvent coming in from the running buffer. This again suggests high permeability of the commercial membranes.

The results suggest that, these commercial membranes are not as robust as hydrogel membranes for electrophoretic separation application.

TABLE 6

Functional test results for PVA separation membranes in comparison to PAm separation membranes

| Batch No | Target IgG transfer (%) | | | Actual IgG transfer (%) | Target EEO | Actual EEO | Protein recovery (%) | Comments |
| | 1000 kDa | 250 kDa | 200 kDa | | | | | |
|---|---|---|---|---|---|---|---|---|
| SPVA-1 | 57 ± 11 | 12 ± 5 | 6 ± 4 | 4.5 ± 1 | <1.5 | 0.3 | 79 | Pass for 200 kDa |
| SPVA-2 | 57 ± 11 | 12 ± 5 | 6 ± 4 | 6 ± 1 | <1.5 | 0.2 | 86 | Pass for 200 kDa |
| SPVA-3 | 57 ± 11 | 12 ± 5 | 6 ± 4 | 5 ± 1 | <1.5 | 0.5 | 79 | Pass for 200 kDa |
| SPVA-4 | 57 ± 11 | 12 ± 5 | 6 ± 4 | 8.4 ± 2 | <1.5 | 0 | 89 | Pass for 250 kDa |
| SPVA-5 | 57 ± 11 | 12 ± 5 | 6 ± 4 | 15 ± 3 | <1.5 | 0 | 97 | Pass for ≥250 kDa |
| SPVA-6 | 57 ± 11 | 12 ± 5 | 6 ± 4 | 21 ± 5 | <1.5 | 1 | 99 | Pass for >250 kDa |
| Control 200 kDa | 57 ± 11 | 12 ± 5 | 6 ± 4 | 4.8 ± 1 | <1.5 | 0 | 77 | Pass for 200 kDa |
| Control 250 kDa | 57 ± 11 | 12 ± 5 | 6 ± 4 | 12 ± 2 | <1.5 | 0 | 80 | Pass for 250 kDa |
| Control 1000 kDa | 57 ± 11 | 12 ± 5 | 6 ± 4 | 50 ± 1 | <1.5 | 1 | 77 | Pass for 1000 kDa |

(EEO = electroendosmosis)

Example 7

Functional Testing of Comparative Membranes

Two types of commercial membranes were obtained from Sterlitech: 1. Polycarbonate (PCT), 0.01 micron and 2. Polyethersulfone (PES), 0.03 micron ultrafiltration membrane. The membranes were tested for their suitability for separating biological molecules using Gradiflow electrophoresis technology.

Figure 16:
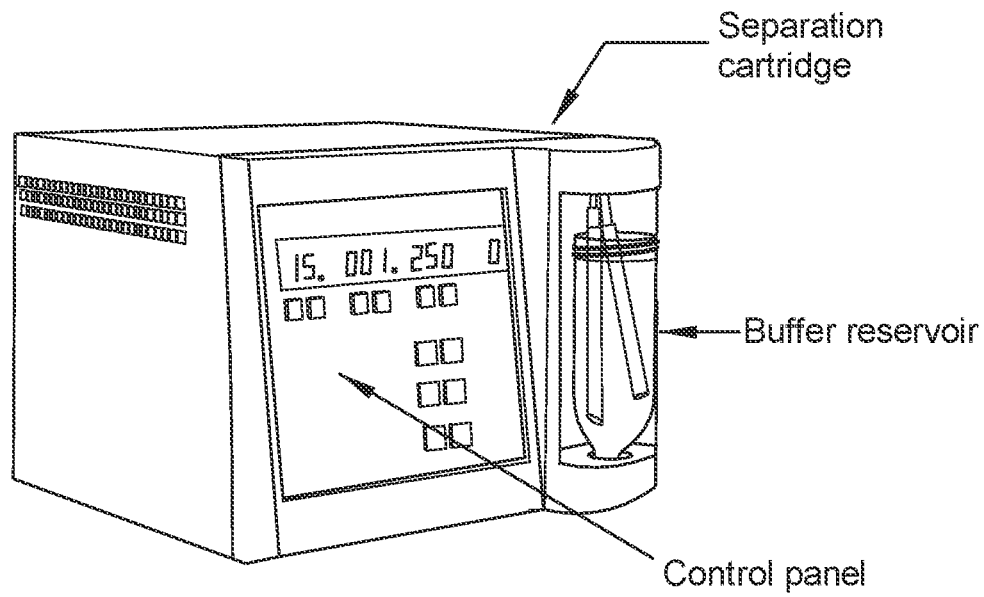
FIG. 16: MF10 electrophoresis separation apparatus.

The tests were carried out using Gradiflow MF10 apparatus (FIG. 16). A 0.5 mg/mL stock solution of bovine insulin (5 kDa, Sigma Aldrich) was prepared in Tris-Borate buffer (pH: 8.4), A MF10 membrane cartridge was prepared, comprising a commercial membrane PCT in the separation position sandwiched between two PAm restriction membranes. Tris-borate buffer was circulated in the buffer tank and kept cold. The functional tests were carried out using an electric potential of 20 V and 200 V with the positive Example 8

Stability Studies on PVA Restriction Membranes

Stability testing experiments were carried out to determine the shelf life of PVA restriction membranes, with PAm membranes used as a control. Long term stability studies were scheduled to determine the shelf life of the PVA membrane (Table 7). The test batch (PVA 38-39) and a control batch (PAm membrane) were stored at three different temperatures: (i) 2-8° C. real time study (standard/recommended storing temperature); (ii) ~22° C. intermediate/accelerated study (storage at room temperature) and (iii) 37° C. accelerated study. The control was tested at 2-8° C. and 37° C. The performance of the product was tested at each time point by functional test using Gradiflow MF10 apparatus (FIG. 16). A 0.5 mg/mL stock solution of bovine insulin (5 kDa, Sigma Aldrich) was prepared in Tris-Hepes buffer (pH: 8.4), A MF10 membrane cartridge was prepared, comprising a PVA restriction membrane in the separation position sandwiched between two PAm restriction membranes. Tris-Hepes buffer was circulated in the buffer tank and kept cold. The functional tests were carried out using an electric potential of 150 V with the positive electrode configured at S2. The protein solution was placed in S1 (sample chamber) and Tris-Hepes buffer in S2 (harvest chamber). The samples in S1 and S2 were harvested after 30 minutes and the protein concentration in both S1 and S2 was measured to calculate percentage transfer of the protein. The functional test for the control was performed at same conditions but with the PVA restriction membrane at the separation position replaced with a PAm restriction membrane.

TABLE 7

Stability schedule for new PVA restriction membranes batch PVA 38-39. X-Indicates a functional test was performed at that time point and storage condition.

| Testing date | Test batch: PVA 38-39 | | | Control batch: PAm | |
|---|---|---|---|---|---|
| | 2-8° C. | ~22° C. | 37° C. | 2-8° C. | 37° C. |
| 21 Jan. 2016 | | | X | | X |
| 4 Feb. 2016 | | X | X | | X |
| 11 Feb. 2016 | X | | | | |
| 18 Feb. 2016 | | | X | | X |
| 25 Feb. 2016 | | | | X | |
| 3 Mar. 2016 | | X | X | | X |
| 17 Mar. 2016 | | | X | | X |
| 31 Mar. 2016 | | | X | | |
| 14 Apr. 2016 | X | | | | |
| 28 Apr. 2016 | | X | | | |
| 12 May 2016 | | | | X | |
| 26 May 2016 | | X | | | |
| 9 Jun. 2016 | X | | | X | |
| 29 Sep. 2016 | X | | | X | |
| 19 Jan. 2017 | X | | | X | |
| 11 May 2017 | X | | | X | |

Figure 17:
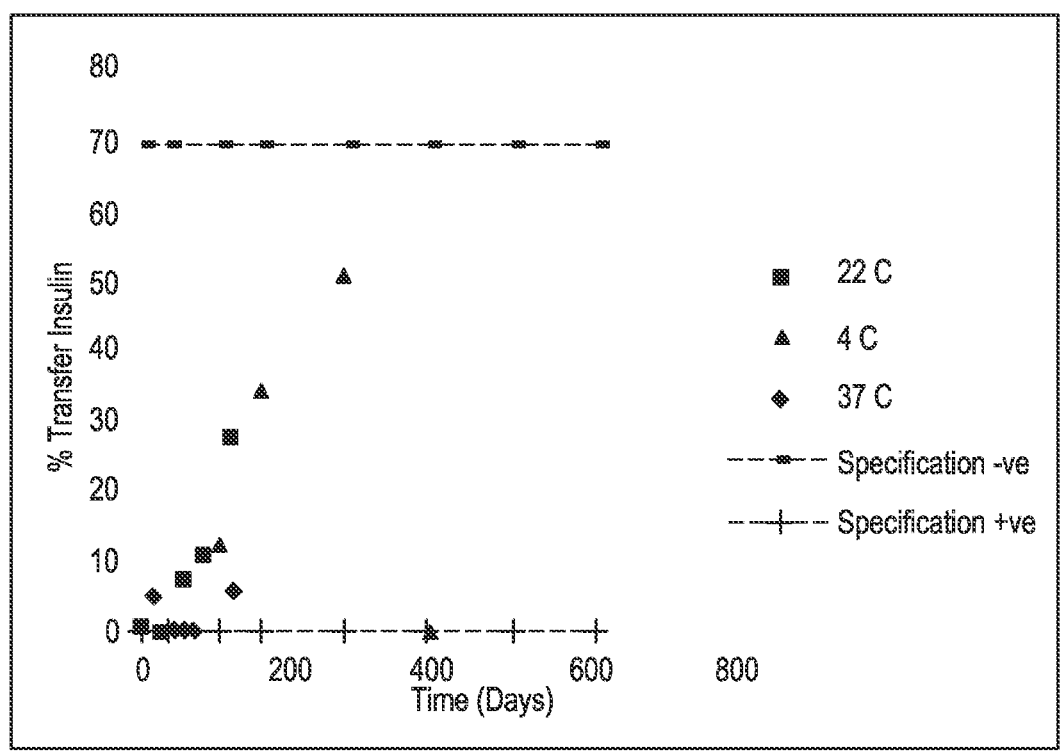
FIG. 17: Functional test results for PVA (38-39) restriction membrane.
Figure 18:
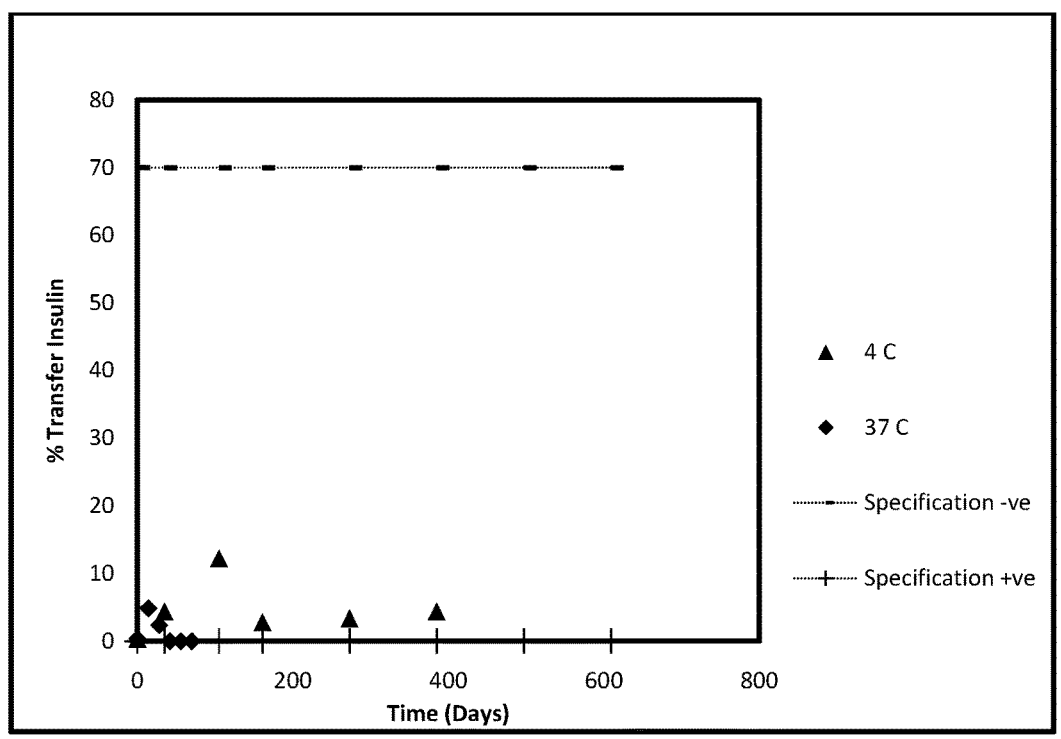
FIG. 18: Functional test results for PAm1104B restriction membrane.

The functional tests results are shown in Table 8. The results show that the PVA restriction membrane performance is comparable to standard PAm restriction membranes and meets the specifications at each time point. The results are plotted in FIGS. 17 and 18.

TABLE 8

Functional test for new PVA restriction membranes batch PVA 38-39 and control PAm1104B.

| Storage condition | Time (Days) | Test batch (PVA 38-39) | | Control (PAm) | |
|---|---|---|---|---|---|
| | | Insulin transfer (%) | EEO | Insulin transfer (%) | EEO |
| 37° C. | 0 | 0.83 | 0 | 0.36 | 0 |
| | 14 | 5.42 | 0 | 4.87 | 0 |
| | 28 | 0 | 0 | 2.37 | 0 |
| | 42 | 0 | 0 | 0 | 0 |
| | 56 | 0 | 0 | 0 | 0 |
| | 70 | 0 | 0 | 0 | 0 |
| | 119 | 5.7 | | | |
| 22° C. | 0 | 0.83 | 0 | | |
| | 28 | 0 | 0 | | |
| | 56 | 7.6 | 0 | | |
| | 84 | 10.97 | | | |
| | 119 | 27.61 | 0 | | |
| 4° C. | 0 | 0.83 | 0 | 0.36 | 0 |
| | 35 | 0.4 | 0 | 4.37 | 0 |
| | 105 | 12.6 | 0 | 12.2 | 0 |
| | 161 | 34.74 | 0 | 2.79 | 0 |

TABLE 8-continued

Functional test for new PVA restriction membranes batch PVA 38-39 and control PAm1104B.

| Storage condition | Time (Days) | Test batch (PVA 38-39) | | Control (PAm) | |
|---|---|---|---|---|---|
| | | Insulin transfer (%) | EEO | Insulin transfer (%) | EEO |
| | 273 | 50.9 | 0 | 3.34 | 0 |
| | 385 | 0 | 0 | 4.37 | 0 |

In view of the results shown above, at all stability time points analysed the quality control specifications for the PVA restriction membrane were met.

Accordingly, the real time data obtained to date demonstrates the PVA restriction membrane is stable for 12.8 months at 2-8° C., and for 3.9 months at 22° C. and 37° C.

Extrapolation of the accelerated condition data may be used to predict the stability duration of the PVA restriction membrane. Generally chemical reaction rates (first order reactions) may double with each 10° C. increase in temperature, thus accelerated stability predictions can be made according to formula derived from the Arrhenius equation (http://rtsf.msu.edu/assets/files/Genomics/Assays_Stability):

$$\text{Predicted stability} = \text{Accelerated stability} \times 2^{\Delta T/10}$$

Where $\Delta T$ is the difference between the normal/standard storage temperature and the sample storage temperature. The greater the difference, the less reliable the prediction.

Taking a conservative estimate from the accelerated study data, the extrapolated stability of the PVA restriction membrane is 16 months at 2-8° C.

Based on all of the above data a shelf-life of 8 months at 2-8° C. (approximately 30% less than real time study results and 50% less than predicted) can be expected.

The invention claimed is:

1. A method of using at least one physically cross-linked biocompatible polymeric membrane in the separation of one or more macromolecules and/or cells by electrophoresis, wherein the membrane comprises poly (vinyl alcohol) (PVA) and an additional polymer, selected from the group consisting of poly(ethylene glycol) (PEG) and poly(N vinylpyrrolidone) (PVPON).

2. The method of claim 1, wherein the membrane is a hydrogel.

3. The method of claim 1, wherein the membrane has a neutral net charge.

4. The method of claim 1, wherein the macromolecules are selected from the group consisting of proteins, peptides, DNA and RNA.

5. The method of claim 1, wherein the membrane is a restriction membrane having a molecular weight cut off (MWCO) less than about 15 kDa.

6. The method of claim 5, wherein the restriction membrane has a molecular weight cut off (MWCO) of less than 5 kDa.

7. The method of claim 5, wherein the restriction membrane is prepared by a casting and annealing method.

8. The use method of claim 7, wherein the method comprises the steps of:
polymer solution preparation;
casting in appropriate casting unit;
drying of the membrane;
annealing at appropriate temperature in an oven; and
cooling and storage.

9. The method of claim 5, wherein the restriction membrane comprises a support substrate.

* * * * *